United States Patent [19]
Hudlicky

[11] Patent Number: 5,834,606
[45] Date of Patent: Nov. 10, 1998

[54] SYNTHESIS OF CONDURITOL EPOXIDES AND AZIRIDINES AND METHODS OF USING SUCH TO SYNTHESIZE HIGHER DISACCHARIDES

[75] Inventor: Tomas Hudlicky, Gainesville, Fla.

[73] Assignee: Genencor International, Inc., Rochester, N.Y.

[21] Appl. No.: 750,191

[22] PCT Filed: Jun. 14, 1995

[86] PCT No.: PCT/US95/07601

§ 371 Date: Feb. 11, 1997

§ 102(e) Date: Feb. 11, 1997

[87] PCT Pub. No.: WO95/35303

PCT Pub. Date: Dec. 28, 1995

[51] Int. Cl.$^6$ .................. C07D 203/26; C07H 17/04; C07H 11/00; C07G 17/00
[52] U.S. Cl. .................. 536/16.1; 536/16.8; 536/124; 548/961; 568/811; 568/822; 568/832
[58] Field of Search .................. 536/16.8, 16.1, 536/124; 568/811, 822, 832; 548/961

[56] References Cited

PUBLICATIONS

Zipperer et al, Chem. Ber., vol. 171, (1988), pp. 757–780.

Ley et al, SYNLETT (1992) pp. 291–292 "Microbial Oxidation in Synthesis: Preparation of Pseudo–alpha–D–glucopyranose from Benzene".

Paulsen et al, Chemical Abstract, vol. 112, No. 139199, (1990) "Cyclit Reactions".

*Primary Examiner*—John Kight
*Assistant Examiner*—Raymond Covington
*Attorney, Agent, or Firm*—Kirsten A. Anderson

[57] ABSTRACT

There are described novel coupling reactions useful for the preparation of cyclitol and/or carbohydrate conjugates and carbocyclic analogs thereof. Such coupling reactions employ epoxides and/or aziridines described herein as electrophilic recipients of other cyclitol or carbohydrate units. Also provided are certain novel compounds.

8 Claims, No Drawings

SYNTHESIS OF CONDURITOL EPOXIDES AND AZIRIDINES AND METHODS OF USING SUCH TO SYNTHESIZE HIGHER DISACCHARIDES

This patent application claims priority to U.S. Ser. No. 08/261,586 filed Jun. 17, 1994, under 35 U.S.C. §120.

FIELD OF THE INVENTION

This invention relates to novel processes for the synthesis of certain conduritol epoxides and aziridines and the use of these epoxides and aziridines to synthesize various or higher disaccharides such as conjugates of cyclitols and/or carbohydrates and their carbocyclic analogs (C-analogs), as well as various heteroatom-linked conjugates such as N-, S- or O-linked conjugates. This invention also relates to certain novel compounds useful as synthons and/or as therapeutic agents useful in treating various disease in a mammal.

BACKGROUND OF THE INVENTION

The expression of arene cis-diols was originally discovered and described by Gibson 24 years ago (Gibson, D. T.; Hensley, M.; Yoshioka, H.; Mabry, J. J. *Biochemistry*, 1970, 9, 1626). Since that time, use of such arene cis-diols in enantiocontrolled synthesis of oxygenated compounds has gained increasing acceptance by those skilled in the art. Many examples of their applications to the total synthesis of carbohydrates, cyclitols, and oxygenated alkaloids can be found in the literature; however, much of the work done within this area has been with the more traditional approach of attaining optically pure compounds from the carbohydrate chiral pool. (Hanessian, S. in *Total Synthesis of Natural Products: The Chiron Approach*; Pergamon: Oxford, 1983).

The synthesis of glycoconjugates has attracted considerable attention recently [(a) Borman, S., *C&E News* 1994, 72, (9), 37; (b) Glycotechnology conference, San Francisco, 1993]. Higher saccharides such as the gangliosides GM3 and sialyl Lewis x both of which are proposed to be involved in malignancy and intercellular adhesion, trans-cell membrane signal transduction and regulation of cell growth have been the subject of intense focus [(a) Danishefsky, S. J.; McClure, K. F.; Randolph, J. T.; Ruggeri, R. B. *Science* 1993, 260, 1307; (b) Liu, K. K. -C.; Danishefsky, S. J. *J. Am. Chem. Soc.* 1993, 115, 4933] by chemical as well as enzymatic means [Ichikawa, Y.; Lin, Y. -C.; Dumas, D. P.; Shen, G. -J.; Garcia-Junceda, E.; Williams, M. A.; Bayer, R.; Ketcham, C.; Walker, L. E.; Paulson, J. C.; Wong, C. -H. *Am. Chem. Soc.* 1992, 114, 9283]. The current chemical and/or enzymatic synthesis of these compounds is arduous at best giving rise to a growing body of high yielding, selective, chemical and enzymatic glycosidation methodologies [(a) Raghavan, S.; Kahne, D. A one-step synthesis of the ciclamycin trisaccharide. *J. Am. Chem. Soc.*, 1993, 115, 1580 and the references therein.; (b) Frazer-Reid, B.; Zugan, W.; Andrews, W.; Skowronski, E. Torsional effects in glycoside reactivity: saccharide couplings mediated by acetate protecting groups. *J. Am. Chem. Soc.*, 1991, 513, 1434.; (c) Frazer-Reid, B. n-Pentenyl glycosides in organic chemistry: a contemporary example of serendipity. *Synlett*, 1992, 927.; (d) Veeneman, G. H.; van Leeuwen, S. H.; van Boom, J. H. An efficient thioglycoside-mediated formation of α-glycosidic linkages promoted by iodonium dicollidine perchlorate. *Tetrahedron Lett.*, 1990, 31, 274.; (e) Kondo, H.; Achi, S.; Ichikawa, Y.; Halcomb, R. C.; Ritzen, H.; Wong, C. -H. Glycosyl phosphites as glycosidation reagents: scope and mechanism. *J. Org. Chem.*, 1994, 59, 864.; (f) Toshima, K.; Nozaki, Y.; Inokuchi, H.; Nakata, M.; Tatsuta, K.; Kinoshita, M. A new entry for the controlled synthesis of 2,6-dideoxy oligosaccharides. *Tetrahedron Lett.*, 1993, 34, 1611]. However, these glycosidation methods are incompatible if the glycosidic donor is to be a carba-sugar and, therefore, would not be useful if a fully carbocyclic oligosaccharide analog were required. Thus, the carbocyclic analogs of these types of compounds are generally unattainable by currently available methods, unless long and arduous routes from carbohydrates are employed [see generally: Hanessian supra].

Whereas the carbocyclic analogs of simple sugars are known (Suami, T.; Ogawa, S. *In Advances in Carbohydrate Chemistry and Biochemistry*; Tipson, R. S.; Horton, D., Eds.; *Academic*: New York, 1990; Vol. 48, p 21; Ley, S. V.; Yeung, L. L. *Synlett* 1992, 291) an attempt at rational and exhaustive design of higher members is absent in the literature.

The present invention alleviates the problems associated with prior chemical or enzymatic synthesis for making cyclitol and carbohydrate conjugates and/or C-analogs thereof by providing methods and useful synthons such as cyclitol conjugates and aziridines which are specifically useful in pseudo-sugar couplings so that semi- and/or fully carba-analogs of carbohydrates can be prepared.

SUMMARY OF THE INVENTION

Therefore, one aspect of this invention relates to biocatalytic methods of synthesis for various conjugates of cyclitols and carbohydrates and their C-, N-, S- or O-linked conjugates. Specifically the conjugates made by the present invention have the formula (1)

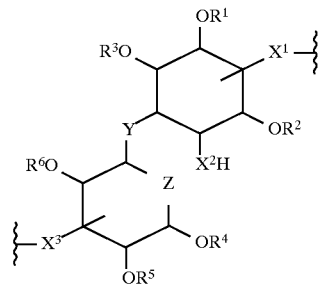

wherein:
$X^1$–$X^3$ independently are $CH_2$, O, NH, or S;
Y is $CH_2$, O, NH, or S;
Z is $CH_2$, O, NH, or S; and
$R^1$–$R^6$ independently are any alcohol protecting group.

Another aspect of the present invention relates to the synthesis and use of cyclitol epoxide (2) and cyclitol aziridine (3) as electrophilic recipients of other cyclitol or C-sugar units in the coupling reactions described herein.

Cyclitol epoxide (2) has the formula:

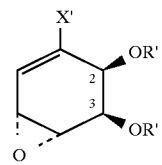

wherein:
X' is H, halogen, CN, alkyl (branched or unbranched C1–C5), aryl (substituted or unsubstituted aromatic) or a heteroatom (wherein the heteroatom may be alone or in a straight chain or ring structure); and
each R' is independently any alcohol protecting group; provided that the alcohols at C2 and C3 need not be protected with the same protecting group.

Aziridine (3) has the formula:

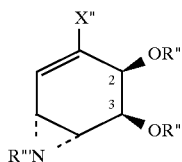

wherein:
X" is H, halogen, CN, alkyl (branched or unbranched C1–C5), aryl (substituted or unsubstituted aromatic) or a heteroatom (wherein the heteroatom may be alone or in a straight chain or ring structure);

each R" is independently any alcohol protecting group; provided that the alcohols at C2 and C3 need not be protected with the same protecting group; and R'" is H, CBZ, tosyl or any substituted or unsubstituted arylsulfonic acid amide, benzyl or $CO_2Me$.

Compound 2, its synthesis, and use as a synthon are described in commonly owned U.S. patent application Ser. No. 07/974,057 incorporated herein by reference. Compound (3) is a novel aziridine and, therefore, another aspect of this invention relates to novel compounds of the formula (3).

DETAILED DESCRIPTION OF THE INVENTION

The present invention relies on understanding and controlling the sites of potential coupling of electrophiles 2 and 3 with nucleophiles. In the general structure 4 (encompassing such electrophiles), there are three possible pathways to

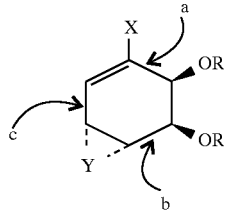

wherein:
X=H, Cl, Br, I, F
Y=O, NTs, NCBZ, NH
R=C(CH$_3$)$_2$, C=O, alkyl, acyl open such electrophiles: a, b, and c. Path b is precluded by stereoelectronic effects, whereas path a and c are subject to normal $S_N$ and $S_{N'}$ arguments as described in the literature on the chemistry of vinyloxiranes. To date, the opening at sites a or c with carbon nucleophiles has been attained only with acetylide anion [Ley, S. V.; Yeung, L. L. *Synlett* 1992, 291–292]. The chemistry of vinylaziridines in general has been limited to their rearrangements to pyrrolines, which involves $S_{N'}$ opening and reclosure with iodide [Hudlicky, T.; Reed, J. W. In *Comprehensive Organic Synthesis*; Paquette, L. A., Ed.; Pergamon: Oxford; Vol. 5, Chapter 8.1]. Ones example of a cuprate addition to vinyl aziridines has been recently reported. [Ibuka, T., et al. *Angew. Chem. Int. Ed. Engl.*, 1994, :33, 652]. The preparation of 3 and its nucleophilic opening tendencies thus remained unknown until the present disclosure.

For the synthesis of glycoconjugates and especially their C-analogs that may offer complementary biological activities, it is desirable that the sites a and c be controlled equally well for heteroatom as well as carbon nucleophiles. For the synthesis of higher saccharides it is also desirable that such opening generate only one nucleophilic group at any given time so that it is available for the next reaction.

Thus the present invention describes the initial model studies necessary to establish the regio- and stereocontrol of nucleophilic opening for 2 and 3. From these initial models, cyclitol and conduramine conjugates such as 5, 6, and 7 as well as their further functionalization to compounds such as 8, 9, and 10 have been made demonstrating that further attachment of protected cyclitol and sugar units is possible in a controlled manner.

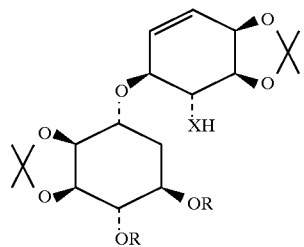

5. X = O
6. X = NTs
7. X = NH
(each R may be Me, Bz, H or any other alcohol protecting group)

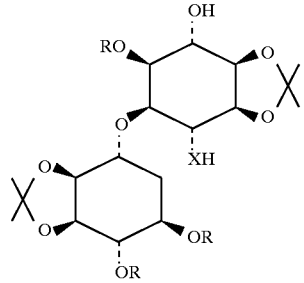

8. X = O
9. X = NTs
10. X = NH
(each R may be Me, Bz, H or any other alcohol protecting group)

The demonstration of the present invention with regard to the synthesis of compounds 5–10 is merely illustrative of the present invention. Those skilled in the art will readily understand the implications of this methodology as it relates to preparation of any cyclitol or carbohydrate conjugate.

In addition, the preparation of fully carbocyclic analogs of the aforementioned compounds (5–10) are described herein, and their synthesis is envisioned by the present invention. Synthesis of these fully carbocyclic analogs rely on the coupling of an organometallic moiety such as 11, which can be derived from dehydroshikimate 12 (Scheme 1).

Scheme 1

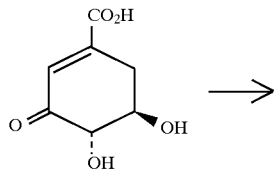

12

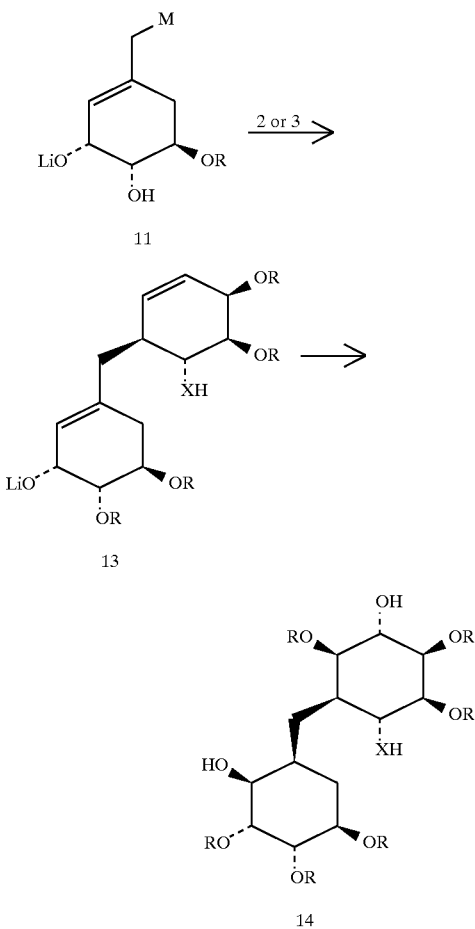

Scheme 1: [R and X are as defined above for compound 1]

Although the present disclosure outlines model studies and reactivity trends of synthons 2 and 3 toward carbon nucleophiles, it also serves as a stereoelectronic model for the union of heteroatom nucleophiles with compounds 2 or 3 to produce higher saccharides and their C-analogs and various heteroatom-linked conjugates. Compounds such as 13 or its hydroxylated analog 14 [derived by methods disclosed in U.S. Pat. No. 5,306,846 and in several publications: (a) hudlicky, T.; Reed, J. W. In *Advances in Asymmetric Synthesis*: A. Hassner, Ed.; JAI Press: Greenwich, Conn., 1994; in press; (b) Hudlicky, T.; Rulin, F.; Tsunoda, T.; Luna, H.; Andersen, C.; Price, J. D. *Isr. J. Chem.* 1991, 31, 229; (c) Hudlicky, T.; Luna, H.; Olivo, H. F.; Andersen, C.; Nugent, T.; Price, J. D. *J. Chem Soc. Perkin Trans.* 1 1991, 2907] are inaccessible by methods currently employed for the synthesis of higher saccharides. Recent disclosures [(a) Ley, S. V.; Yeung, L. L. *Synlett* 1992, 997; (b) Reddy, K. K.; Falck, J. R.; Capdevila, J. *Tetrahedron Lett.* 1993, 34, 7869] indicate that such compounds may be useful as antidiabetic agents and in general cell-signalling mechanisms.

The currently disclosed invention capitalizes on some of the previously disclosed techniques of operationally simple provision of sugar or cyclitol units from arene cis-diols as is outlined in Scheme 2 [see also: (a) Hudlicky, T.; Mandel, M.; Rouden, J.; Lee, R. S.; Bachmann, B.; Dudding, T.; Yost, K. J.; Merola, J. S. *J. Chem. Soc., Perkin Trans.* 1 1994, 1553; (b) Hudlicky, T.; Rouden, J.; Luna, H.; Allen, S. *J. Am. Chem. Soc.* 1994, 116, 5099; (c) Hudlicky, T.; Olivo, H. F.; McKibben, B. *J. Am. Chem. Soc.* 1994, 116, 5108] and provides conceptual guide as to the oligomerization of these units as outlined in Scheme 3.

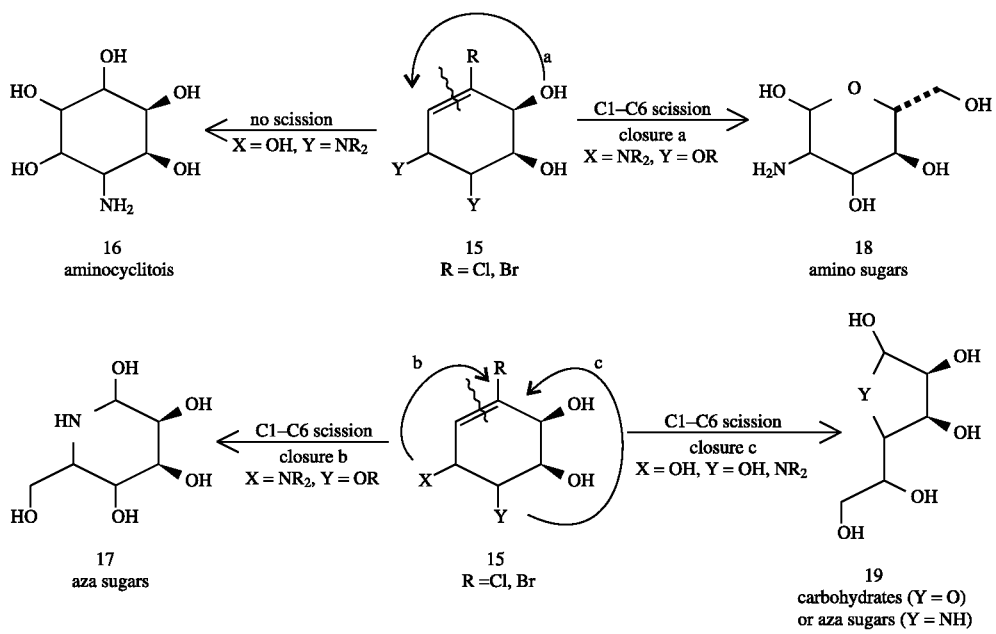

Scheme 3

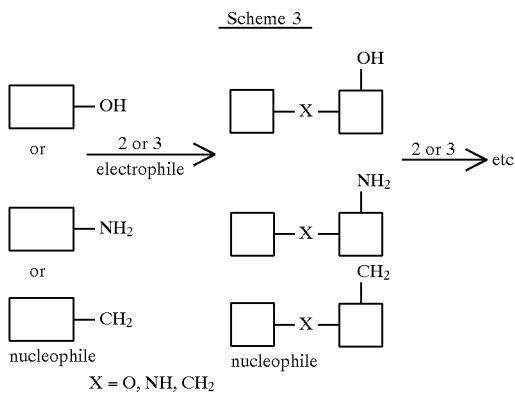

Scheme 3 illustrates in a very simplistic manner the overall impact of the present invention, whereby electrophiles such as 2 and 3 are opened at controlled sites, by heteroatom or carbon nucleophiles (under appropriate conditions) resulting in the coupling of the electrophile (conduritol epoxide or aziridine 2 or 3) with the heteroatom or carbon atom which newly coupled nucleophile can repeatedly be coupled with similar electrophiles resulting ultimately in any number of carbohydrates or glycoconjugates.

Of additional significance in the current invention is the stepwise control of introduction of substituents made possible by differential protection as well as stereoelectronic differences between olefins in the cyclitol units. In other words, when protecting the electrophile with different groups and protecting the nucleophile with different groups, only one nucleophilic and electrophilic site will be available at a time. For example, as shown in Scheme 4, opening epoxide 20 with benzyl alcohol affords; cyclitol 21 which is now disposed to act as a nucleophile when exposed to epoxide 22. After coupling 21 and 22 there is only one hydroxyl in 23 and two olefins, which can be successfully functionalized to either cis or trans protected diols by methods disclosed in U.S. Pat. No. 5,306,846, the disclosure of which is incorporated herein by reference, Hudlicky, T.; Reed, J. W. In *Advances in Asymmetric Synthesis*; A. Hassner, Ed.; JAI Press: Greenwich, Conn., 1994; in press. For the synthesis of further conjugates this process may be repeated provided only one nucleophilic entity is present.

Scheme 4

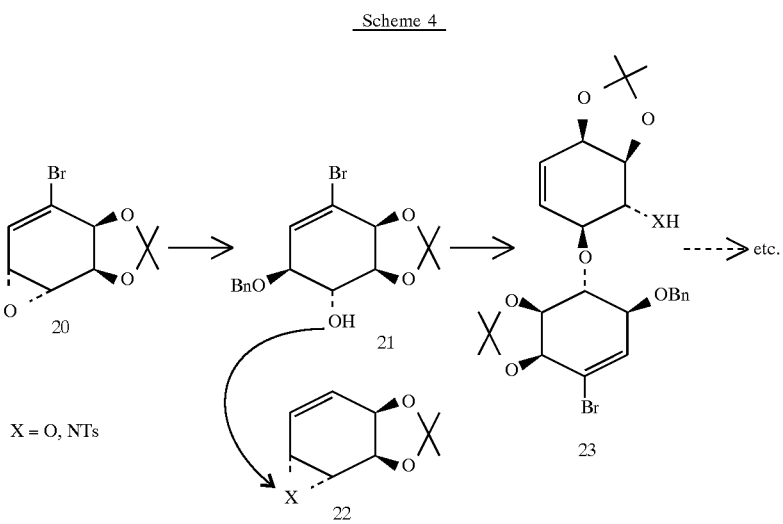

Further studies indicate that a methylcyclohexyl moiety can be effectively added to, with both epoxides and aziridines, to provide models for C-saccharide conjugates of the type shown below. This concept has been demonstrated by the synthesis of gala-quercitol-L-chiro-inositol conjugate starting from aromatic precursors, such as by Scheme 5 shown below.

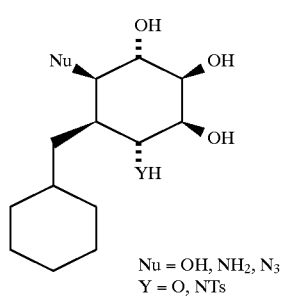

Nu = OH, NH$_2$, N$_3$
Y = O, NTs

Reaction between the epoxide (Carless, H. A. J., *Tetrahedron Lett.*, 1993, 33, 6379) and the secondary alcohol (Hudlicky, T.; Luna, H.; Olivo, H. H.; Anderson, C.; Nugent, T.; Price, J. D.; *J. Chem. Soc. Perkin Trans.* 1, 1991, 2907; Hudlicky, T.; Mandel, M.; Rouden, J.; Lee, R. S.; Bachmann, B.; Dudding, T.; Yost, K. J.; Merola, J. S.; *J. Chem. Soc. Perkin Trans.* 1, 1994, 1553) both readily accessible from halobenzenes via microbial oxidation ((a) Gibson, D. T.; Koch, G. R.; Kallio, R. E.; *Biochemistry*; 1968, 7, 2653 (b) Gibson, D. T.; Hensley, M.; Yoshioka, H.; Mabry, J. J.; *Biochemistry*, 1970, 9, 1626)gave in the presence of boron trifluoride, the coupled adduct in 75% yield (Scheme 5). Predominant reaction of the vinyl epoxide at the allylic position follows observations in our laboratories (Hudlicky, T.; Fan, R.; unpublished results; (a) Hudlicky, T.; Konigsberger, K.; Xinrong, T.; *J. Org. Chem.* 1994, 59, 4037 (b) Hudlicky, T.; Rouden, J.; Luna, H.; Allen, S.; *J. Am. Chem. Soc.*, 1994, 116, 5099) which indicate the general preference for nucleophiles to attack the allylic position of substrates such as the vinyl epoxide syn to the isopropylidene group. Treatment of the di-alkene (of Scheme 5) with osmium tetroxide, continuously recycled by 4-methyl morpholine N-oxide, gave the bis-hydroxylated species in good yield, which was subsequently converted to the polyoxygenated conjugate (gala-quercitol-L-chiro-inositol) under acidic catalysis.

sibilities regarding substitution patterns, identity of protecting groups, stereochemistry and enantiomeric constitution are well understood to those skilled in the art. These parameters can be controlled at the stage of each monomeric unit.

As used in the present invention "suitable or appropriate solvents" include, but are not limited to, water, water miscible solvents such as dialkylketones with 2–4 carbon atoms, lower alcohols having 1–3 carbon atoms, cyclic ethers, and ethers with 2–6 carbon atoms, or mixtures thereof.

As used herein "reducing agent" includes, but is not limited to, a transition metal reagent, a hydride reagent or trialkylsilane such as tributyltinhydride or tris (trimethylsilyl) silane, sodium naphthalide, or sodium amalgam. These reducing agents may be used in combination with radical initiation agents such as UV light and/or AIBN or dibenzoylperoxide or a similar initiator.

As used herein "acid catalyst" includes, but is not limited to, mineral acids such as HCl; Lewis acids; organic acids such as p-toluenesulfonic acid; acid ion exchange resins such as Amberlyst 15, Amberlyst IR 118, Amberlite CG-50, Dowex 50 X 8-100 (all are commercially available from Aldrich), or similar acidic ion exchange resins.

As used herein "alkaline catalyst" includes, but is not limited to, alkaline metal hydroxide or alkaline earth metal hydroxides such as LiOH, NaOH, KOH, or $Ba(OH)_2$; car-

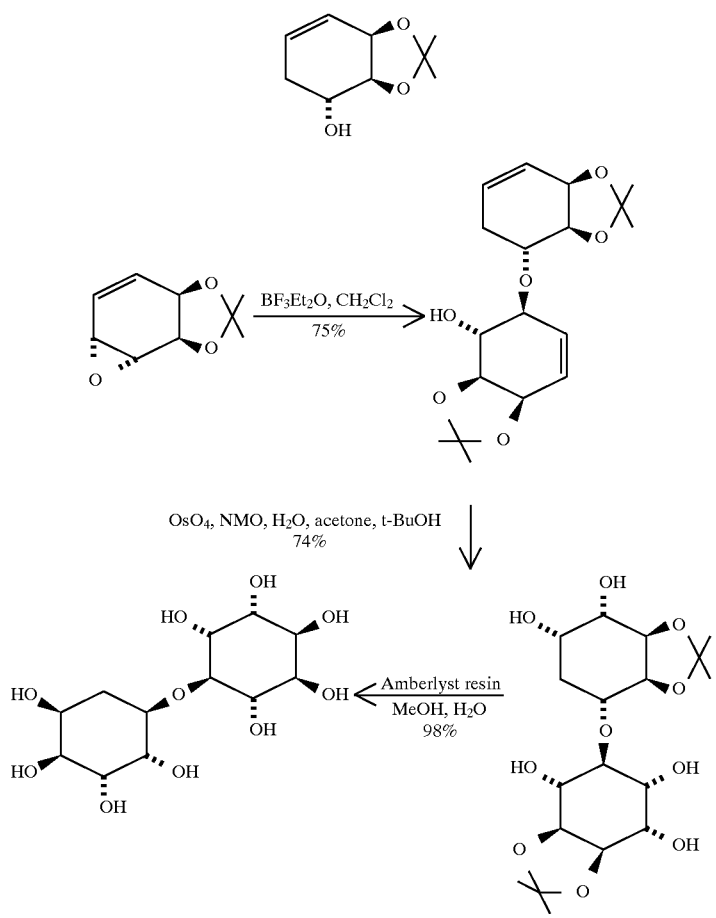

Scheme 5

The current invention facilitates the design and synthesis of many higher cyclitol conjugates and their C-analogs unavailable by traditional methods. The combinational posbonate or bicarbonate of alkaline metal such as $Na_2CO_3$ or $K_2CO_3$; $Al_2O_3$ or basic ion exchange resin such as Amberlite IRA-400, Amberlyst A26, Amberlyst A21, Dowex 1X2-200 or other ion exchange resins.

As used herein "an alcohol protecting group" includes, but is not limited to, H, acetate, acetonide, alkyl (C1–C5), aryl (any aromatic group substituted or unsubstituted), esters, ethers, silylethers, arylsulfonylamides, t-butyldimethylsilyl, benzyl, benzoates or any other alcohol protecting group known to those skilled in the art.

As used herein "an appropriate organometallic reagent" includes, but is not limited to, those described in Tables 1 and 2. Such reagents are commonly known to those skilled in the art. These are shown in Table 1 by the general formula RM where R is methyl, methylcyclohexyl, or phenyl, and M is Mg, Cu, Sn, Pd.

As used herein "carbon or heteroatom conjugate" means a C-, N-, O- or S-linked conjugate or analog of a given compound, such as a C-, N-, O- or S-linked analog of cyclitols and/or carbohydrates.

Suitable conditions, including solvents and temperatures are listed in Tables 1 and 2 and include, but are not limited to, the types of solvents and temperature ranges respectively. Temperature ranges implies −100° C. to +160° C.

General Synthesis of Electrophiles 2 and 3

Epoxide 2 and aziridine 3 can be generated following the biocatalytic production of cis-diols derived from substituted benzenes. However, the coupling methods of the present invention will work regardless of the method used to make the electrophiles 2 and 3. The synthesis of epoxide 2 is described in U.S. Pat. No. 5,306,846 and U.S. patent application No. 07/974,057, the disclosure of each is incorporated herein by reference; and Hudlicky, T., Rulin, F., Tsunoda, T., Luna, H., Andersen, C., Price, J. D. *Isr. J. Chem.* 1991, 31, 229. The aziridine is a novel compound and its synthesis is described both generally and in detail in the Experimental section herein. General methods for aziridine formation are found in Yamada, Y., Yamamoto, T., Okawara, M. Chem. Lett. 1975, 361; Evans, D. A., Faul, M. M., Bilodeau, M. T. *J. Orgr. Chem.* 1991, 56, 6744; and Evans, D. A., Faul, M. M., Bilodeau, M. T., Anderson, B. A., Barnes, D. M. *J. Am. Chem. Soc.* 1993, 115, 5326.

Use of Synthons 2 and 3

Compounds such as 14, 23 and 24 are generated by exposing either epoxide 2 or aziridine 3 to nucleophilic monomers such as 11 derived from dehydroshikimate. These initial targets are identified and fully deprotected to obtain corresponding compounds containing all free hydroxyl or amino groups. These compounds may be used in the treatment of diabetes or other cell-signalling mediated diseases.

Partially protected dimers such as 14, 23 and 24 may then be used in further coupling to generate trimers which can subsequently be coupled to form tetramers, etc. The details of methods available for the coupling of sugars or cyclitol monomers are provided below.

Table 1 lists the major products obtained thus far by opening of epoxides 2a and 2b with organometallic reagents of the general formula RM where R is methyl, methylcyclohexyl, or phenyl, and M is Mg, Cu, Sn, Pd. The Table is not intended to limit the present invention, particularly since these reactions are disclosed to serve as model systems for C-disaccharide synthesis, as, for example, opening of an epoxide (2a) with methyl organometallics to yield 25. Compound 25 can be used for the synthesis of methylquercitol (deoxy-C-mannose) derivative 45 as shown below.

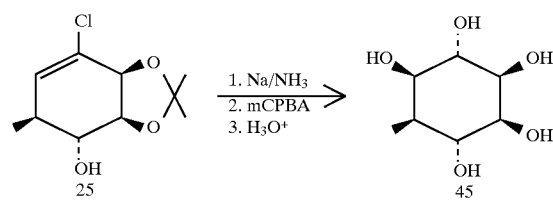

By the same token, the use of methylcyclohexyl residues provides C-disaccharide model Compound 46 by the reaction shown below:

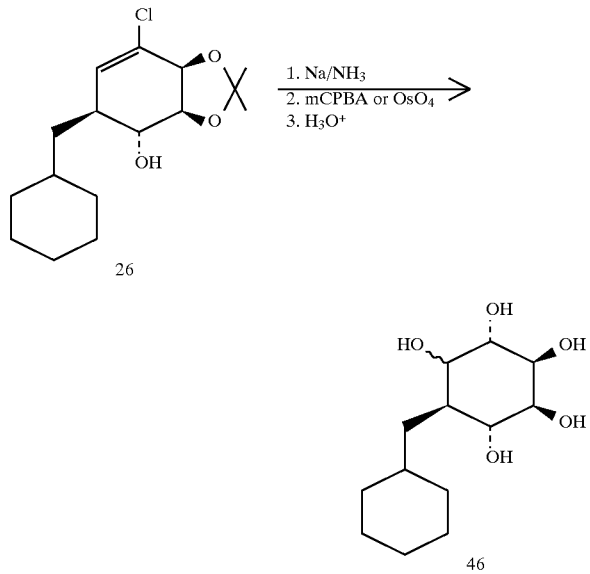

Further application of the coupling methods of this invention is illustrated by the reaction below showing an azido or amino derivative of 46, namely 47 and 48 respectively, available from 26 by the sequences shown:

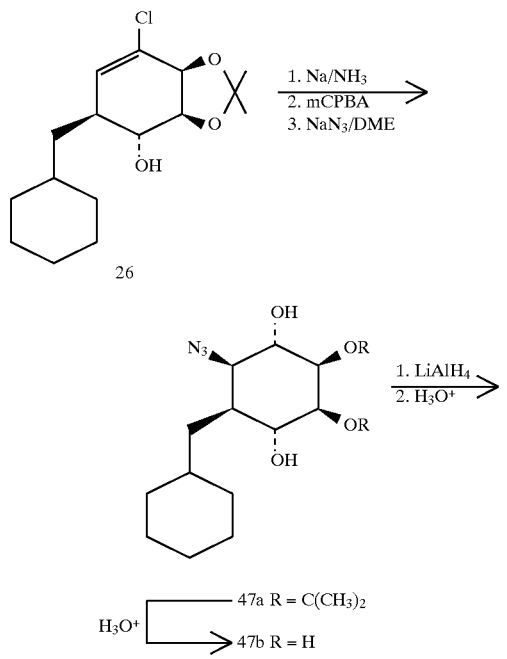

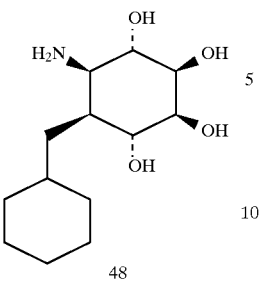

48

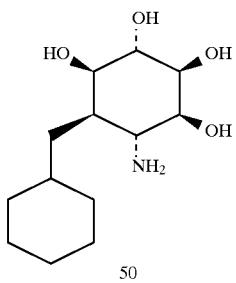

50

A trisaccharide can be made by the coupling methods described herein, for example, 49 is available from 27 by full deprotection. It should be noted that isomers 32 and 33 (shown in Table 1) are ideally suited as disaccharide models also, albeit in different configurations than the C-mannose 44.

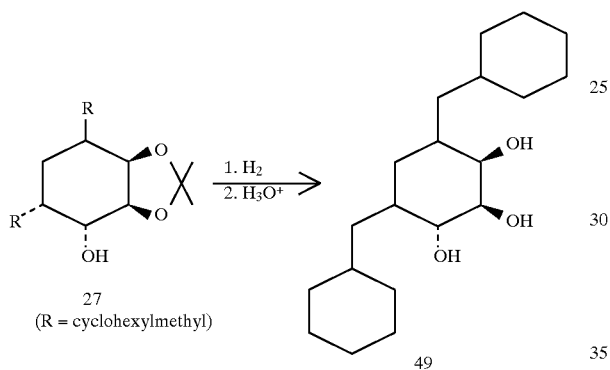

27
(R = cyclohexylmethyl)

49

Table 2 lists the major products obtained thus far by opening aziridines 3a and 3b. Table 2 is not intended to limit the present: invention, particularly since these reactions are provided as a model system for coupling reactions. One skilled in the art will recognize various embodiments of the present invention such as those described herein.

Aminoinositol compounds of the type 50 are accessible as shown in the examples below:

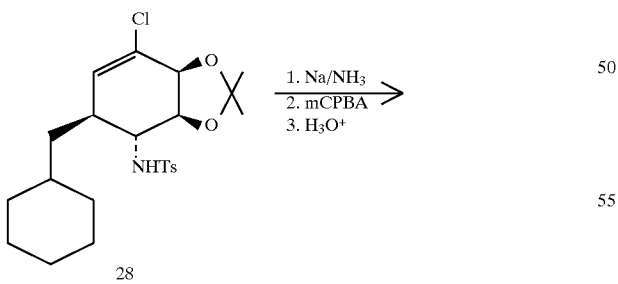

28

Phenyl (CuCN) cuprate was used to form product 43 in an improved yield of 49%. It is contemplated that using the methods of the present invention the compound pancratistatin 53, a known anticancer agent, can be made from the known compound 51 (C. H. Heathcock, et al. *Tetrahedron Lett.*, 1992, 6775) based on the conversion of compound 51 to 52 as shown.

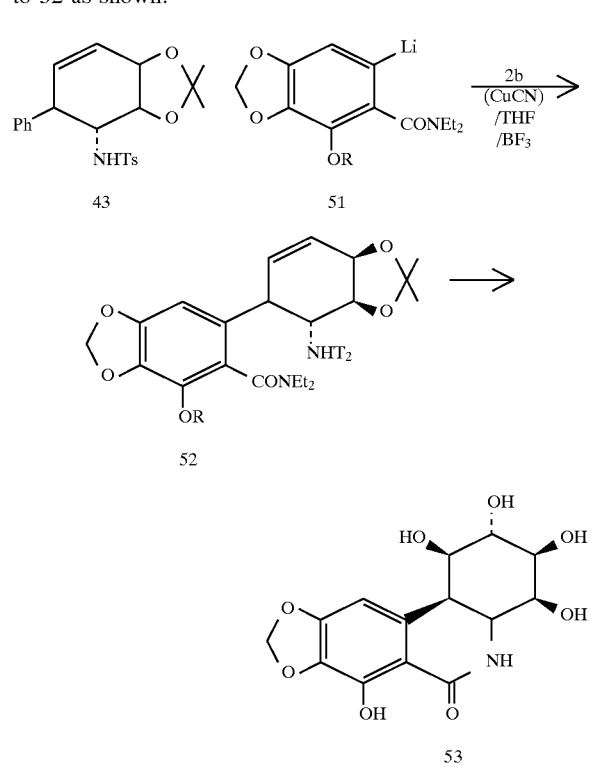

It is further contemplated that the coupling methods described herein can be employed in pseudo-sugar coupling such that semi- or fully carba-analogs of the general type 55 or 57 or other heteroatom conjugates of 54 and 56 could be made.

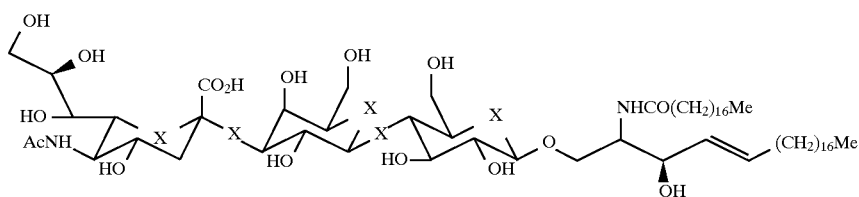

54. X = O GM3
55. X = CH₂

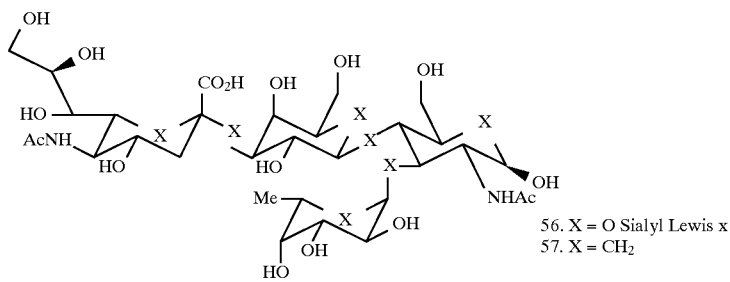

56. X = O Sialyl Lewis x
57. X = CH₂

The ganglioside GM3 54 and its metabolic precursors are important starting points for the biosynthesis of other gangliosides. Gangliosides in general have been proposed as being involved in malignancy and intercellular adhesion, trans-cell membrane signal transduction and regulation of cell growth. $GM_3$ itself is known to be active in governing epidermal growth factor and platelet-derived growth factor receptors, and importantly is found in much higher concentrations in tumor cells. Sialyl Lewis x 56 is an important cellular surface oligosaccharide involved in cellular adhesion processes and also found in increased amounts in patients suffering from breast, pancreatic and gastrointestinal cancer. The interest in these two structurally similar oligosaccharides has stimulated several chemical and enzymatic total syntheses.

For these reasons there should be great interest in the synthesis of carba-oligosaccharide analogs of $GM_3$ or sialyl Lewis x. We propose that access to these types of semi- or fully-carbocyclic mimics should be attainable by coupling nucleophilic carba-sugars with standard glycosidic donors or electrophilic carba-sugar epoxides and aziridines.

The precise choice of O-atom replacement within GM3 (see 55 above) will await the synthesis of the first such derivative containing O-linked carba-sugars and its biological evaluation. Following this result, rational thought and design will be applied to the definition of the next specific target. We believe that the demonstration of the capability to synthesize such carba-analogs in a controlled manner will open the way for the preparation of any isomer or isostere of these and other saccharides.

Exemplary reactions for vinyloxiranines and vinylaziridines are shown in Tables 1 and 2 respectfully. It is understood that the skilled artisan, reading this disclosure will be able to alter the exact electrophile, nucleophile, and conditions of the reactions. Therefore, these are provided to illustrate the present invention and should not be construed as limiting the invention.

TABLE 1

EXEMPLARY REACTIONS OF VINYLOXIRANES

| ELECTROPHILE | NUCLEOPHILE/ CONDITIONS | PRODUCT (% YIELD) |
|---|---|---|
| 2a | MeMgBr/10% CuI THF/−78° to −40° C. | 25 (58) |
| 2a | RMgBr/10% CuI THF/−78° to 0° C. R = cyclohexylmethyl | 26 (39) |

TABLE 1-continued

EXEMPLARY REACTIONS OF VINYLOXIRANES

| ELECTROPHILE | NUCLEOPHILE/ CONDITIONS | PRODUCT (% YIELD) |
|---|---|---|
| 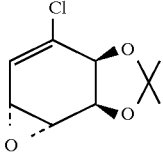<br>2a | $R_2$CuLi<br>$Et_2$O/THF/−78° to −40° C.<br>R = cyclohexylmethyl | 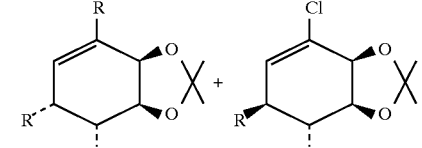<br>27 (14)   28 (4) |
| 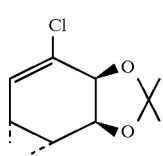<br>2a | $Ph_2$CuLi<br>$Et_2$O/0° C. | 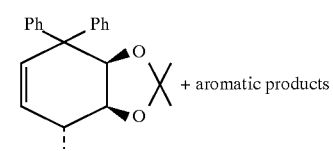 + aromatic products<br>29 (8) |
| 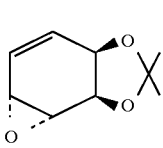<br>2b | MeMgBr/10% CuI<br>$Et_2$O/THF | 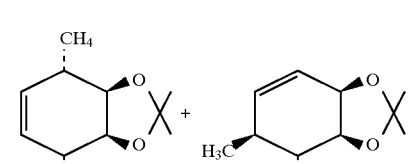<br>30 (35)   31 (11) |
| 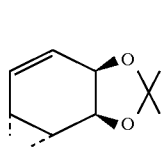<br>2b | RMgBr/10% CuI<br>THF/−78° to −10° C.<br>R = cyclohexylmethyl | 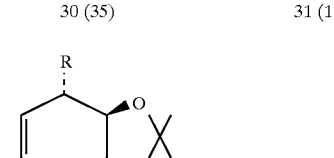<br>32 (83) |
| 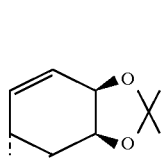<br>2b | $R_2$CuLi<br>$Et_2$O/THF/−78° to −40° C.<br>R = cyclohexylmethyl | 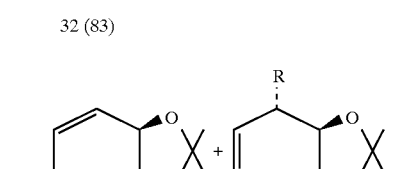<br>33 (37)   34 (5) |
| 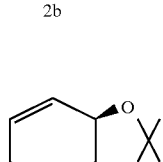<br>2b | $Me_2$CuLi<br>$Et_2$O/THF/−78° C. | 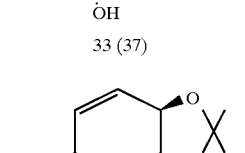<br>35 (30) |
| 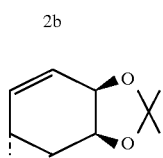<br>2b | PhSnMe$_3$/Pd(0)<br>DMF/$H_2$O/RT | 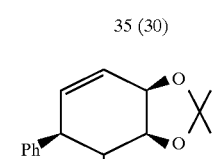<br>36 (10) |

TABLE 2

EXEMPLARY REACTIONS OF VINYLAZIRIDINES

| ELECTROPHILE | NUCLEOPHILE/ CONDITIONS | PRODUCT (% YIELD) |
|---|---|---|
| 3a | Ph$_2$CuLi, THF/−78° C. to RT | 37 (57) |
| 3a | Ph$_2$Cd, THF/50° C. | 38 (50) |
| 3a | Ph$_2$Zn, THF/Et$_2$O/RT | 37 + 38, 3:1 (36) |
| 3a | R$_2$CuLi, THF/Et$_2$O/−78° to −40° C., R = cyclohexylmethyl | 39 (89) |
| 3a | CH$_3$MgBr/CuI, THF/Et$_2$O/−45° C. | 40 (53) |
| 3b | R$_2$CuLi, Et$_2$O/THF/−78° to −40° C., R = cyclohexylmethyl | 41 (76) |
| 3b | Ph$_2$CuLi, THF/−78° to RT | 42 (38) + 43 (6) |

TABLE 2-continued

EXEMPLARY REACTIONS OF VINYLAZIRIDINES

| ELECTROPHILE | NUCLEOPHILE/ CONDITIONS | PRODUCT (% YIELD) |
|---|---|---|
| 3b | Ph₂CuCNLi₂ THF/−78° C. | 43 (23) |
| 3b | CH₃MgBr/CuI THF/Et₂O/−45° C. | 44 (29) |

EXPERIMENTAL

General: All reactions were carried out in an argon atmosphere with standard techniques for the exclusion of air and moisture. Glassware used for moisture sensitive reactions was flame dried under vacuum. Tetrahydrofurane, diethylether (ether) and toluene were distilled from Na benzophenone ketyl. $^1$H NMR spectra were recorded at 270 MHz or 400 MHz, $^{13}$C NMR spectra at 50 MHz, 68 MHz or 100.6 MHz. Flash column chromatography was performed on Merck silica gel (grade 60, 230–400 mesh). Elemental analysis was performed by Atlantic Microlabs, Norcross, Ga.

General procedure for the formation of aziridines 3a and 3c: A mixture of 5 equivalents (eq.) of (1S, 2S)-3-halo-1,2-isopropylidenedioxycyclohexa-3,5-diene, 1 eq. of p-tosyliminophenyliodinane (PhI=NTs) and 0.08 eq. of copper acetyl acetonate (Cu(acac)₂) in 10 mL mmol$^{-1}$ of CH₃CN was stirred at room temperature (rt). After consumption of PhI=NTs the mixture was filtered through a pad of silica gel and concentrated in vacuo. The crude product was recrystallized from hexane/ethyl acetate.

EXAMPLE 1

(1R,4s,5s,6R)-3-Chloro-4,5-isopropylidenedioxy-7-(4'-methyl-phenyl)sulfonylbicyclo[4.1.0]hept-2-ene (3a)

The compound was obtained in 20.5% yield from (1S, 2S)-3-chloro-1,2-isopropylidenedioxycyclohexa-3,5-diene following the general procedure set forth above (reaction time 18 h): white solid; mp 202°–203° C. (hexane, ethyl acetate); $[\alpha]_D^{25}$ −75.5° (c=1.54, CHCl₃); $^1$H NMR (270 MHz, CDCl₃) δ 7.82(dm, J=8.2 Hz, 2H), 7.37(dm, J=8.2 Hz, 2H), 6.09 (dd, J=4.9, 1.2 Hz, 1H), 4.65 (ddd, J=6.6, 1.8, 0.7 Hz, 1H), 4.30 (dd, J=6.6, 1.0 Hz, 1H), 3.44 (dd, J=6.5, 1.8 Hz, 1H), 3.34 (dt, J=0.6, 6.5 Hz, 1H), 2.46 (s, 3H), 1.41 (s, 3H), 1.38 (s, 3H); $^{13}$C NMR (68 MHz, CDCl₃) δ 145.3 (C), 138.05 (C), 134.41 (C), 130.06 (2CH), 128.07 (2CH), 119.96 (CH), 111.72 (C), 73.04 (CH), 71.68 (CH), 37.17 (CH), 36.74 (CH), 27.51 (CH₃), 26.07 (CH₃), 21.74 (CH₃); MS (CI+) m/z (rel. intensity) 356 (M+H$^+$) (3), 340 (6), 298 (27), 262 (23), 200 (36), 155 (100), 142 (36), 114 (60), 91 (43). Anal. Calcd. for C₁₆H₁₈ClNO₄: C, 54.00; H, 5.12; N, 3.94. Found: C, 53.92; H, 5.12; N, 3.86.

EXAMPLE 2

(1R,4R,5S,6R)-3-Bromo-4,5-isopropylidenedioxy-7-(4'-methylphenyl)-sulfonylbicyclo[4.1.0]hept-2-ene (3c)

From 10.52 g (45.52 mmol) of (1S, 2S)-3-bromo-1,2-isopropylidenedioxycyclohexa-3,5-diene, 3c (1.97 g, 54% yield) was obtained following the general procedure described above (reaction time 1 h): white solid; mp 206°–207° C. (hexane, ethyl acetate); $[\alpha]_D^{25}$ −33.7° (c=1.05 CHCl₃); $^1$H NMR (270 MHz, CDCl₃) δ 7.82 (dm, J=8.2 Hz, 2H), 7.37 (dm, J=8.2 Hz, 2H), 6.35 (dd, J=4.9, 1.3 Hz, 1H), 4.64 (ddd, J=6.5, 1.7, 0.6 Hz, 1H), 4.34 (dd, J=6.5, 1.2 Hz, 1H), 3.44 (dd, J=6.5, 1.8 Hz, 1H), 3.28 (dd, J=6.5, 5.1 Hz, 1H), 2.46 (s, 3H), 1.42 (s, 3H), 1.38 (s, 3H) ; $^{13}$C NMR (100.6 MHz, CDCl₃) δ 145.1 (C), 134.1 (C), 129.92 (2CH), 129.89 (C), 127.9 (2CH), 123.9 (CH), 111.5 (C), 73.8 (CH), 71.4 (CH), 37.4 (CH), 36.4 (CH), 27.4 (CH₃), 26.1 (CH₃), 21.6 (CH₃); MS (CI+) m/z (rel. intensity) 400 (M+H$^+$) (2), 384 (1.5), 372 (1.5), 344 (23), 314 (12), 262 (29), 244 (11), 228 (7), 187 (29), 155 (100), 108 (60), 91 (31); HRMS (CI+) m/z calcd for (C₁₆H₁₈BrNO₄S+H) 400.0218, found 400.0231.

EXAMPLE 3

1R,4R,5S,6R)-4,5-Isopropylidenedioxy-7-(4'-methylphenyl) sulfonylbicyclo[4.1.0]hept-2-ene (3b)

A mixture of 617 mg (1.54 mmol) of 3c, 896 mg (3.09 mmol) of tributyltin hydride and 23 mg of AIBN in 25 mL of toluene was stirred under reflux. After 3 h, another 20 mg of AIBN was added and reflux was continued for 2.5 h. The mixture was washed with excess saturated KF aqueous solution, and the organic layer was dried over Na₂SO₄. Removal of solvent and column chromatography (silica gel, 3:1 hexane/EtOAc) afforded 288 mg (58%) of 3b: white solid; $^1$H NMR (270 MHz, CDCl₃) δ 7.82 (dm, J=8.2 Hz, 2H), 7.35 (br.d, J=8.0 Hz, 2H), 5.95 (ddd, J=10.2, 4.4, 1.7 Hz, 1H), 5.76 (dd, J=10.2, 2.4 Hz, 1H), 4.54 (dd, J=6.7, 1.5 Hz, 1H), 4.39 (dt, J=6.7, 1.0 Hz, 1H), 3.37 (dd, J=6.5, 1.8 Hz, 1H), 3.27 (dd, J=6.5, 4.7 Hz, 1H), 2.46 (s, 3H), 1.37 (s, 3H), 1.34 (s, 3H); $^{13}$C NMR (68 MHz, CDCl₃) δ 144.8, 134.6, 132.4, 129.8 (2C), 127.9 (2C), 120.9 110.7, 70.6, 69.3, 36.4, 35.5, 27.8, 26.1, 21.6.

EXAMPLE 4

(1R,2R,5S,6S)-4-Chloro-5,6-isopropylidenedioxy-2-methylcyclohex-3-en-1-ol (25)

0.65 mL (1.95 mmol) of 3M methylmagnesium bromide in ether was added to a suspension of 39 mg (0.20 mmol) of CuI in 7 mL of ether at −40° C. The mixture was stirred for 15 min before it was cooled to −78° C. A solution of 307 mg (1.52 mmol) of 2a in 3 mL of ether was added and the mixture was stirred at −78° C. for 2.5 h, then warmed slowly to −40° C. After 2 h, the reaction was quenched with 3 mL of saturated ammonium chloride solution, and the reaction mixture was extracted with ether (3×20 mL). The combined ether layers were dried over $Na_2SO_4$, and concentrated in vacuo. The residue was chromatographed on silica gel, eluted with 2:1 hexane/ethyl acetate to afford 293 mg (58%) of 25: colorless oil; bp 100°–110° C. (0.1 mm, Kugelrohr); $[\alpha]_D^{25}$ −21° (c=1.74, $CHCl_3$); IR (neat) 3460, 2990 2930, 2880, 1375, 1240, 1210, 1160, 1080, 1065, 1050, 925, 870 $cm^{-1}$; $^1H$ :NMR (270 MHz, $CDCl_3$) δ 5.79 (d, J=2.0 Hz, 1H), 4.60 (dd, J=6.4, 1.4 Hz, 1H), 4.05 (dd, J=8.9, 6.3 Hz, 1H), 3.34 (dt, J=1.8, 9.0 Hz, 1H), 2.55 (d, J=2.3 Hz, 1H), 2.26 (m, 1H), 1.57 (s, 3H), 1.45 (s, 3H), 1.18 (d, J=7.1 Hz, 3H); $^{13}C$ NMR (68 MHz, $CDCl_3$) δ 145.3 (C), 138.06 (C), 134.41 (C), 130.06 (2CH), 128.07 (2CH), 119.96 (CH), 111.72 (C), 73.04 (CH), 71.68 (CH), 37.17 (CH), 36.74 (CH), 27.51 ($CH_3$), 26.07 ($CH_3$), 21.74 ($CH_3$); MS (EI, 70 eV) m/z (rel. intensity) 203 ($M^+$—$CH_3$) (100), 143 (87), 115 (81), 79 (54); HRMS (CI+) m/z calcd for ($C_{10}H_{15}ClO_3$+H) 219.0788, found 219.0794.

EXAMPLE 5

(1R,2R,5S,6S)-(4-Chloro-5,6-isopropylidenedioxy-2-cyclohexylmethylcyclohex-3-en-1-ol (26)

To a suspension of 364 mg (14.97 mmol) of Mg and a small crystal of iodine in 3 mL of THF a solution of 1.6 mL of cyclohexylmethyl bromide in 15 mL of THF was added over 1 h and the mixture was stirred at rt for 1.5 h. The resulting Grignard reagent was added into a suspension of 160 mg (0.84 mmol) of CuI in 4 mL of THF at −40° C. The mixture was stirred for 15 min, then cooled to −78° C., and a solution of 1.707 g (8.42 mmol) of 2a in 8 mL of THF was added dropwise. The reaction mixture was warmed slowly to 0° C. and stirred at 0° C. for 3 h. The reaction was quenched with 5 mL of saturated $NH_4Cl$ solution and the mixture was extracted with ethyl acetate (3×15 mL). The combined organic layers were dried over $Na_2SO_4$. Evaporation of the solvent and chromatography (hexane/EtOAc) afforded 995 mg (39%) of 26 .

$^1H$ NMR (270 MHz, $CDCl_3$)δ 5.91 (d, J=2.10 Hz, 1H), 4.59 (dd, J=6.28, 1.24 Hz, 1H), 4.05(dd, J=8.59, 6.30 Hz, 1H), 3.38 (dt, J=8.80, 2.84 Hz, 1H), 2.28 (bs, 1H), 2.24 (m, 1H), 1.53 (s, 3H), 1.42 (s, 3H), 0.70~1.90 (m, 13H). $^{13}C$ NMR (68 MHz, $CDCl_3$) δ 131.41 (CH), 127.75 (C), 110.34 (C), 79.91 (CH), 75.89 (CH), 72.97 (CH), 38.64 (CH), 38.39 ($CH_2$), 34.73 (CH), 34.43 ($CH_2$), 32.50 ($CH_2$), 28.29 ($CH_3$), 26.56 ($CH_2$), 26.31 ($CH_2$), 26.12 ($CH_2$), 25.99 ($CH_3$).

EXAMPLE 6

(1R,2R,5R,6S)-2,4-Di(cyclohexylmethyl)-5,6-isopropylidenedioxy-cyclohex-3-en-1-ol (27)

To a suspension of 215 mg (31 mmol) of lithium in 12 mL of THF at −30° C. was added 0.865 mL (6.2 mmol) of cyclohexylmethyl bromide at −30° C. The mixture was stirred 2 h before it was cannulated to a suspension of 590 mg (3.10 mmol) of cuprous iodide in 3 mL of ether precooled to −35° C. The mixture was stirred at −40° C. for 40 min and cooled to −78° C., and a solution of 203 mg (1.00 mmol) of 2a in 3 mL of THF was added. The resulting mixture was stirred at −78° C. for 2 h and then allowed to warm up to −40° C. before the reaction was quenched with 5 mL of saturated aqueous $NH_4Cl$ solution. The aqueous layer was extracted with ethyl acetate (3×10 mL), and the combined organic phases were dried over $Na_2SO_4$. Removal of solvent and flash column chromatography (silica gel, hexane/ethyl acetate, 4:1) afforded 52 mg (14%) of 27 and 12 mg (4%) of 28.

For 27, $^1H$ NMR (270 MHz, $CDCl_3$) δ 5.35 (d, J=3.55 Hz, 1H), 4.47 (d, J=6.09 Hz, 1H), 4.24 (t, J=6.15 Hz, 1H), 3.90 (bs, 1H), 2.52 (bs, 1H), 2.19 (dd, J=13.96, 5.40 Hz, 1H), 1.41 (s, 3H), 1.39 (s, 3H). $^{13}C$ NMR (68 MHz, $CDCl_3$) δ 134.32 (C), 127.94 (CH), 108.85 (C), 76.51 (CH), 73.96 (CH), 71.05 (CH), 41.99 ($CH_2$), 38.02 ($CH_2$), 35.29 (CH), 34.98 (CH), 34.99 (CH), 33.87 ($CH_2$), 33.25 ($CH_2$), 32.81 ($CH_2$), 27.73 ($CH_3$), 26.62 (2$CH_2$), 26.32 (2$CH_2$), 25.94 ($CH_3$).

EXAMPLE 7

(1R,5R,6S)-5,6-Isopropylidenedioxy-4,4-diphenylcyclohex-2-en-1-ol (29)

To a suspension of 596 mg (3.12 mmol) of CuI in 5 mL of ether was added 3.5 mL of 1.8M phenyllithium solution at 0° C. The mixture was stirred for 30 min and then a solution of 634 mg (3.13 mmol) of 2a in 5 mL of ether was added. The mixture was stirred at: 0° C. for 2 h and at rt for 8 h before the reaction was quenched with 5 mL of ice water. The aqueous layer was extracted with ethyl acetate (3×15 mL), and the combined organic layers were dried over $Na_2SO_4$. Removal of solvent and column chromatography (silica gel, 2:1 hexane/ethyl acetate) gave 80 mg (8% yield) of 29.

$^1H$ NMR (270 MHz, $CDCl_3$) δ 7.10~7.40 (m, 10H), 6.38 (d, J=9.93 Hz, 1H), 6.11 (dd, J=9.93,3.59 Hz, 1H), 5.01 (d, J=6.75 Hz, 1H), 4.41 (dd, J=6.77,3.74 Hz, 1H), 4.29 (m, 1H), 1.93 (d, J=6.75 Hz, 1H), 1.36 (s, 3H), 1.27 (s, 3H). $^{13}C$ NMR (68 MHz, $CDCl_3$) δ 147.77 (c), 143.43 (C), 136.12 (CH), 129.86 (CH), 129.49 (2CH), 128.56 (2CH), 127.69 (CH), 127.50 (2CH), 126.64 (CH), 126.20 (CH), 108,79 (C), 81.05 (CH), 79.90 (CH), 69.70 (CH), 52.39 (C), 26.62 ($CH_3$), 25.14 ($CH_3$).

EXAMPLE 8

(1R,2S,5R,6S)-5,6-Isopropylidenedioxy-4-methylcyclohex-3-en-1-ol (30) and (1R,2S,5R,6S)-5,6-Isopropylidenedioxy-2-methylcyclohex-3-en-1-ol (31)

To a suspension of CuI (29 mg, 0.15 mmol) in anhydrous ether was added a solution of methylmagnesium bromide (MeMgBr) (0.515 mL, 1.54 mmol) at −40° C. and stirred for 30 min. At −78° C. compound 2b (200 mg, 1.19 mmol) in anhydrous THF (5 mL) was added precooled via cannula and the mixture was warmed slowly to −40° C. and stirred for 2 h at −40° C. MeMgBr (0.25 mL, 0.75 mmol) was added. After 30 min the white suspension was quenched using saturated $NH_4Cl$ solution (20 mL) and the mixture was extracted with $CH_2Cl_2$ (4x). The combined organic phases were washed with brine, dried over $Na_2SO_4$ and concentrated in vacuo. Chromatography (toluene/ethyl acetate, 75:25) afforded 30 (77 mg, 35%) and 31 (24 mg, 11%).

30: colorless oil; $^1H$ NMR (270 MHz, $CDCl_3$) δ 5.75 (ddd, J=9.7, 3.0, 2.2 Hz, 1H), 5.50 (dt, J=9.6, 2.9 Hz, 1H), 4.20 (m, 1H), 4.00 (dd, J=7.8, 6.2 Hz, 1H), 3.81 (t, J=7.3 Hz, 1H), 2.76 (br.s, 1H), 21.7 (m, 1H), 1.48 (s, 3H), 1.36 (s, 3H), 1.24 (d, J=7.2, 1H); $^{13}C$ NMR (68 MHz, $CDCl_3$) δ 131.89, 130.74, 108.88, 81.44, 79.35, 71.90, 35.12, 27.26, 24.75, 18.91.

31: colorless oil; $^1$H NMR (270 MHz, CDl$_3$) δ 5.80 (ddd, J=9.8, 3.5, 2.8 Hz, 1H), 5.65 (br.d, J=9.8 Hz, 1H), 4.57 (m, 1H), 3.96 (dd, J=9.0, 6.3 Hz, 1H), 3.27 (dt, J=2.6, 9.3 Hz, 1H), 2.73 (d, J=2.4 Hz, 1H), 2.13 (m, 1H), 1.48 (s, 3H), 1.37 (s, 3H), 1.14 (d, J=7.1, 1H); $^{13}$C NMR (68 MHz, CDCl$_3$) δ 136.8, 122.4, 109.4, 79.7, 75.3, 72.8, 35.6, 28.4, 25.8, 17.1.

EXAMPLE 9

(1R,4S,5R,6S)-4-Cyclohexylmethyl-5,6-isopropylidenedioxycyclohex-2-en-1-ol (32)

To a suspension of 39 mg (0.20 mmol) of cuprous iodide in 3 mL of THF cooled to −40° C. was added 2.69 mmol of cyclohexylmethyl magnesium bromide. The mixture was stirred at −40° C. for 15 min then cooled to −78° C., when solution of 334 mg (1.99 mmol) of 2b in 4 mL of THF was added. The mixture was warmed to −10° C. with stirring before the reaction was quenched with 5 mL of saturated NH$_4$Cl solution. The aqueous layer was extracted with ethyl acetate (3×15 mL), and the combined organic layers were dried over Na$_2$SO$_4$. The product was purified using column chromatography (silica gel, hexane/ethyl acetate, 3:1) to give 439 mg (83%) of 32.

$^1$H NMR (270 MHz, CDCl$_3$) δ 5.76 (dt, J=9.71,2.57 Hz, 1H), 5.61 (dt, J=9.71, 2.77 Hz, 1H), 4.21 (m, 1H), 3.97 (dd, J=7.66,6.08 Hz, 1H), 3.83 (dd, J=7.51, 6.56 Hz, 1H), 2.58 (bs, 1H), 2.19 (m, 1H), 1.47 (s, 3H), 1.36 (s, 3H). $^{13}$C NMR (68 MHz, CDCl$_3$) δ 130.74 (CH), 130.54 (CH), 108.67 (C), 81.40 (CH), 78.30 (CH), 71.61 (CH), 41.42 (CH$_2$), 37.40 (CH), 35.10 (CH), 33.94 (CH$_2$), 32.81 (CH$_2$), 27.30 (CH$_3$), 26.56 (CH$_2$), 26.25 (CH$_2$), 26.12 (CH$_2$), 24.88 (CH$_3$).

EXAMPLE 10

(1R,2R,5R,6S)-2-Cyclohexylmethyl-5,6-isopropylidenedioxycyclohex-3-en-1-ol (33)

To a suspension of 350 mg (50.4 mmol) of lithium in 17 mL of ether at −30° C. was added 1.395 mL (10.0 mmol) of cyclohexylmethyl bromide at −30° C. The mixture was stirred at −30° C. for 2 h before it was cannulated to a suspension of 952 mg (5.00 mmol) of cuprous iodide in 5 mL of ether precooled to −40° C. The mixture was stirred at −40° C. for 40 min and cooled to −78° C., when a solution of 279 mg (1.66 mmol) of 2b in 4 mL of THF was added. The resulting mixture was stirred at −78° C. for 2 h before the reaction was quenched by 5 mL of saturated aqueous NH$_4$Cl solution. The aqueous layer was extracted with ethyl acetate (3×15 mL), and the combined organic phases were dried over Na$_2$SO$_4$. Removal of solvent and column chromatography (silica gel, CH$_2$Cl$_2$/acetone, 5:1) afforded 165 mg (37%) of 33 and 25 mg (5%) of 32.

EXAMPLE 11

(1R,2R,5R,6S)-5,6-Isopropylidenedioxy-2-methylcyclohex-3-en-1-ol (35)

At −30° C. methyllithium (2.55 mL, 3.57 mmol) was added slowly to a stirred suspension of cuprous iodide (340 mg, 1.78 mmol). After 30 min compound 2b (110 mg, 0.65 mmol) was added precooled by cannula at −78° C. The reaction was quenched after 30 min with saturated NH$_4$Cl solution (10 mL). The mixture was extracted with CH$_2$Cl$_2$ (4x). The combined extracts were washed with brine, dried over MgSO$_4$ and concentrated in vacuo. Chromatography (hexane/ethyl acetate, 67:33) afforded 35 (36 mg, 30%) : colorless oil; $^1$H NMR (270 MHz, CDCl$_3$) δ 5.85 (dd, J=10.0, 4.3 Hz, 1H), 5.77 (ddd, J=10.0, 3.4 Hz, 1H), 4.63 (dd, J=6.1, 3.4 Hz, 1H), 4.20 (dd, J=7.5, 6.2 Hz, 1H), 3.87 (dd, J=7.5, 4.7 Hz, 1H), 2.55 (m, 1H), 1.80 (s, 1H), 1.47 (s, 3H), 1.40 (s, 3H), 1.07 (d, J=7.3, 1H); $^{13}$C NMR (100.6 MHz, CDCl$_3$) δ 135.13, 123.38, 109.03, 76.27, 72.12, 71.61, 33.30, 28.12, 25.87, 14.41.

EXAMPLE 12

(1R,2R,5R,6S)-5,6-Isopropylidenedioxy-2-phenylcyclohex-3-en-1-ol (36)

To a degassed solution of compound 2b (200 mg, 1.19 mmol) in DMF (2.0 mL) and H$_2$O (0.20 mL, 11 mmol) Pd(CH$_3$CN)$_2$Cl$_2$ (15 mg, 0.05 mmol) was added under argon. After 5 min phenyltrimethyltin (344 mg, 1.43 mmol) was added to the orange solution which decolored to a pale yellow. The initially exothermic reaction was cooled to maintain rt. After 10 min more phenyltrimethyltin (160 mg) was added. After complete consumption of 2b (20 min) the black mixture was diluted (CH$_2$Cl$_2$, 30 mL), filtered over Celite®, washed (H$_2$O, brine), dried over Na$_2$SO$_4$, and concentrated in vacuo. Chromatography (hexane/ethyl acetate, 67:33) afforded 36 (29 mg, 10%): white solid; mp. 95°–96° C.; IR (KBr) 3490, 3090, 3040, 3000, 2940, 2880, 1495, 1455, 1382, 1370, 1250, 1160, 1070, 1055, 903, 880, 860, 800, 755, 705 cm$^{-1}$; $^1$H NMR (400 MHz, CDCl$_3$) δ 7.36 (t, J=7.2 Hz, 2H), 7.29 (t, J=7.3 Hz, 1H), 7.25 (d, J=7.2 Hz, 2H), 603 (ddd, J=9.9, 3.7, 3.0 Hz, 1H), 5.88 (dt, J=9.9, 1.2 Hz, 1H), 4.73 (m, 1H), 4.17 (dd, J=8.8, 6.4 Hz, 1H), 3.62 (dt, J=1.2, 9.3 Hz, 1H), 3.28 (ddt, J=9.8, 2.8, 1.5 Hz, 1H), 2.06 (d, J=2.0 Hz, 1H), 1.53 (s, 3H), 1.42 (s, 3H); $^{13}$C NMR (100.6 MHz, CDCl$_3$) δ 140.82, 134.61, 128.78 (2C), 128.38 (2C) 127.29, 124.17, 109.75, 79.02, 75.13, 72.74, 48.22, 28.33, 25.77; MS (Cl+) m/z (rel. intensity) 231 (M$^+$−15) (100), 171 (72), 159 (43), 143 (71), 128 (30), 115 (30), 101 (39), 91 (54).

EXAMPLE 13

(1R,2S,5R,6S)-N-(5,6-Isopropylidenedioxy-2,4-diphenylcyclohex-3-enyl)-(4'-methylphenyl) sulfonamide (37)

Phenyllithium (0.47 mL, 0.84 mmol) was added to a suspension of CuI (80 mg, 0.42 mmol) in anhydrous THF at −40° C. and stirred for 15 min. Compound 3a (50 mg, 0.14 mmol) in anhydrous THF (2 mL) was added precooled by cannula, followed by BF$_3$Et$_2$O (60 mg, 0.42 mmol), and the mixture was stirred and allowed to warm to rt over 12 h. The reaction was quenched using NH$_4$OH solution, solid NH$_4$Cl was added and the mixture was extracted with ether (5x). The combined extracts were washed with brine, dried over MgSO$_4$ and concentrated in vacuo. Chromatography afforded 37 (35 mg, 52%): white solid; mp. 268°–270° C.: [α]$_D^{25}$ −105.2° (c=0.50, CHCl$_3$); $^1$H NMR (270 MHz, CDCl$_3$) δ 7.59 (m, 4H), 7.08–7.41 (m, 10H), 6.34 (d, J=4.8 Hz, 1H), 5.19 (d, J=5.7 Hz, 1H), 4.37 (d, J=6.6 Hz, 1H), 4.27 (dd, J=8.3, 5.5 Hz, 1H), 4.14 (t, J=5.1 Hz, 1H), 3.62 (ddd, J=8.1, 6.6, 5.2 Hz, 1H), 2.40 (s, 3H), 1.38 (s, 3H), 1.14 (s, 3H); $^{13}$C NMR (100.6 MHz, CDCl$_3$) δ 143.19 (C), 138.66 (C), 136.96 (C), 136.45 (C), 136.26 (C), 129.62 (2CH), 129.51 (2CH), 128.63 (2CH), 128.61 (2CH), 128.00 (CH), 127.35 (4CH), 125.97 (2CH), 109.56 (C), 74.21 (CH), 72.98 (CH), 55.26 (CH), 43.92 (CH), 27.28 (CH$_3$), 25.95 (CH$_3$), 21.45 (CH$_3$), MS (CI+) m/z (rel. intensity) (M+H$^+$ not found), 418 (7), 400 (18), 247 (82), 222 (87), 139 (30), 98 (68), 91 (100).

EXAMPLE 14

(1R,5R,6S)-N-(4,4-Diphenyl-5,6-isopropylidenedioxycyclohex-2-enyl)-(4'-methylphenyl)sulfonamide (38)

To a suspension of anhydrous CdCl$_2$ (103 mg, 0.56 mmol) in anhydrous THF (10 mL) phenyllithium (0.62 mL, 1.12 mmol) was added slowly at rt, and the yellow solution was heated at reflux for 45 min. After cooling to rt compound 3a (100 mg, 0.28 mmol) in anhydrous THF (5 mL) was added and the mixture was heated to 55° C. for 27 h. Saturated NH$_4$Cl solution (15 mL) was added and the mixture was extracted with ether (4x). Drying over MgSO$_4$, concentration in vacuo and chromatography (hexane/ethyl acetate, 80:20) afforded 38 (67 mg, 50%): glassy solid; $^1$H NMR (400 MHz, CDCl$_3$) δ 7.65 (dm, J=8.4 Hz, 2H), 7.14–7.39 (m, 12H), 6.53 (dt, J=9.9, 1.1 Hz, 1H), 5.82 (ddd, J=10.0, 5.4, 0.6 Hz, 1H), 5.07 (dd, J=6.1, 1.4 Hz, 1H), 4.37 (dd, J=6.1, 1.4 Hz, 1H), 3.87 (dd, J=9.3,5.3 Hz, 1H), 3.81 (d, J=9.3 Hz, 1H), 2.42 (s, 3H), 1.256 (s, 3H), 1.249 (s, 3H); $^{13}$C NMR (100.6 MHz, CDCl$_3$) δ 146.73 (C), 144.85 (C), 143.57 (C), 138.45 (CH), 138.03 (C), 129.82 (2CH), 129.20 (2CH), 129.02 (2CH), 127.93 (2CH), 127.80 (2H), 127.55 (CH), 127.34 (2CH), 126.59 (CH), 126.40 (CH), 108.67 (C), 80.04 (CH), 78.57 (CH), 52.96 (CH), 50.80 (C), 26.94 (CH$_3$), 25.22 (CH$_3$), 21.76 (CH$_3$); MS (CI+) m/z (rel. intensity) (M+H$^+$ found), 418 (14), 400 (12), 388 (10), 375 (12), 276 (22), 247 (100), 219 (45), 172 (23), 155 (28) 91 (100).

EXAMPLE 15

(1R,2R,5R,6S)-N-[2,4-Di(cyclohexylmethyl)-5,6-isopropylidene-dioxycyclohex-3-enyl]-(4'-methylphenyl)sulfonamide (39)

To a suspension of 193 mg (27.8 mmol) of lithium in 12 mL of ether cooled to −30° C. was added 0.766 mL (5.56 mmol) of cyclohexylmethyl bromide. The mixture was stirred at −30° C. for 2 h and cannulated to a suspension of 529 mg (2.78 mmol) of cuprous iodide in 3 mL of ether precooled to −40° C. After the mixture was stirred at −40° C. for 40 min, it was cooled to −78° C. and a solution of 329 mg (0.92 mmol) of 3a in 5 mL of THF was added. The mixture was stirred at −78° C. for 2 h, then slowly warmed to −40° C. and stirred at −40° C. for 2 h, then quenched with 5 mL of saturated aqueous ammonium chloride and extracted with ethyl acetate (3×15 mL). The combined organic layers were dried over Na$_2$SO$_4$ and concentrated in vacuo. The residue was chromatographed (silica gel, 4:1 hexane/EtOAc) to give 433 mg (89%) of 39.

White solid, mp 192°–193° C.; $^1$H NMR (270 MHz, CDCl$_3$) δ 7.76 (d, J=8.30 Hz, 2H), 7.29 (d, J=8.09, 2H), 5.29 (bs, 1H), 4.46 (d, J=6.28 Hz, 1H), 4.40 (d, J=5.83 Hz, 1H), 4.28 (t, J=5.97 Hz, 1H), 3.38 (q, J=4.51 Hz, 1H), 2.65 (bs, 1H), 2.41 (s, 3H), 2.11 (dd, J=14.26, 5.52 Hz, 1H), 1.82 (dd, J=14.15, 8.56 Hz, 1H), 1.31 (s, 3H), 1.14 (s, 3H), 0.50~1.72 (m, 24H). $^{13}$C NMR (68 MHz, CDCl$_3$) δ 143.43 (C), 137.54 (C), 135.44 (C), 129.65 (2CH), 128.19 (CH), 127.39 (2CH), 109.28 (C), 75.01 (CH), 73.59 (CH), 55.06 (CH), 42.10 (CH$_2$), 38.20 (CH$_2$), 35.29 (CH), 34.55 (CH), 33.87 (CH$_2$), 33.62 (CH$_2$), 33.02 (2CH$_2$), 32.06 (CH), 27.30 (CH$_3$), 26.62 (2CH$_2$), 26.26 (2CH$_2$), 26.06 (CH$_2$), 25.93 (CH$_3$), 21.41 (CH$_3$). Anal. Calcd for C$_{30}$H$_{45}$O$_4$NS:C, 69.86; H, 8.79; N, 2.72. Found: C, 69.92; H, 8.81; N, 2.69.

EXAMPLE 16

(1R,2R,5S,6S)-N-(4-Chloro-5,6-isopropylidenedioxy-2-methylcyclohex-3-enyl)-(4'-methylphenyl)sulfonamide (40)

To a suspension of CuI (14 mg, 0.073 mmol) in anhydrous ether was added a solution of methylmagnesium bromide (MeMgBr) (0.050 mL, 0.15 mmol) at −45° C. and stirred for 30 min. Compound 3a (200 mg, 0.56 mmol) in anhydrous THF (5 mL) was added precooled via cannula and MeMgBr (0.40 mL, 1.20 mmol) was added over 60 min. After 7 h the white suspension was quenched using saturated NH$_4$Cl solution (containing NH$_3$, pH 9) (30 mL) and the mixture was extracted with ether (4x). The combined organic phases were washed with brine, dried over Na$_2$SO$_4$ and concentrated in vacuo. Chromatography (toluene/ethyl acetate, 80:20) afforded 40 (111 mg, 53%): $^1$H NMR (400 MHz, CDCl$_3$) δ 7.79 (dm, J=8.2 Hz, 2H), 7.29 (dm, J=8.7 Hz, 2H), 5.79 (d, J=3.0 Hz, 1H), 5.02 (d, J=8.5 Hz, 1H), 4.50 (dd, J=6.0, 1.4 Hz, 1H), 4.08 (dd, J=7.9, 6.0 Hz, 1H), 3.28 (q, J=8.0 Hz, 1H), 2.45 (s, 1H), 2.19 (ddquintett, J=1.4, 3.1, 7.3 Hz, 1H), 1.282 (s, 3H), 1.258 (s, 3H), 1.13 (d, J=7.2 Hz, 3H); $^{13}$C NMR (100.6 MHz, CDCl$_3$) δ 143.2, 138.3, 132.1, 129.3 (2C), 128.4, 127.2 (2C), 110.3, 77.7, 75.2, 57.2, 36.5, 27.4, 25.8, 21.5, 18.0.

EXAMPLE 17

(1R,4S,5R,6S)-N-(4-Cyclohexylmethyl-5,6-isopropylidene-dioxycyclohex-2-enyl)-(4'-methylphenyl)sulfonamide (41)

To a suspension of 187 mg (26.94 mmol) of lithium in 12 mL of ether at −30° C. was added 0.726 mL (5.20 mmol) of cyclohexylmethyl bromide at −30° C. The mixture was stirred at −30° C. for 2 h before it was cannulated to a suspension of 495 mg (2.60 mmol) of cuprous iodide in 3 mL of ether precooled to −40° C. The mixture was stirred at −40° C. for 40 min and cooled to −78° C., when a solution of 281 mg (0.87 mmol) of 3b in 4 mL of THF was added. The resulting mixture was stirred at −78° C. for 2 h and then allowed to warm to −40° C. before the reaction was quenched with 5 mL of saturated aqueous NH$_4$Cl solution. The aqueous layer was extracted with ethyl acetate (3×15 mL), and the combined organic phases were dried over Na$_2$SO$_4$. Removal of solvent and column chromatography (silica gel, hexane/ethyl acetate, 3:1) afforded 276 mg (76%) of 41.

White solid; mp 138°–139° C.; [α]$_D^{20}$=40.4° (c=0.96, CHCl$_3$); $^1$H NMR (270 MHz, CDCl$_3$) δ 7.79 (d, J=8.25 Hz, 2H), 7.30 (d, J=8.21 Hz, 2H), 5.66 (m, 2H), 4.70 (d, J=5.58 Hz, 1H), 3.81 (m, 2H), 3.58 (m, 1H), 2.42 (s, 3H), 2.22 (bs, 1H), 1.23 (s, 3H), 1.16 (s, 3H), 0.71~1.80 (m, 13H).$^{13}$ C NMR (68 MHz, CDCl$_3$) δ 143.30 (C), 137.48 (C), 132.34 (CH), 132.34 (CH), 129.49 (CH), 128.00 (CH), 127.51 (CH), 108.79 (C), 78.36 (CH), 78.18 (CH), 54.81 (CH), 41.74 (CH$_2$), 37.03 (CH), 35.10 (CH), 33.80 (CH$_2$), 32.99 (CH$_2$), 27.24 (CH$_3$), 26.55 (CH$_2$), 26.23 (CH$_2$), 25.19 (CH$_3$), 21.30 (CH$_3$).

EXAMPLE 18

(1R,4R,5R,6S)-N-(5,6-Isopropylidenedioxy-4-phenylcyclohex-2-enyl)-(4'-methylphenyl) sulfonamide (42) and (1R,2R,5R,6S)-N-(5,6-Isopropylidenedioxy-2-phenylcyclohex-3-enyl)-(4'-methylphenyl) sulfon-amide (43)

Method A: With lithium diphenylcuprate: 2.36 mL of 1.8M phenyllithium solution was added slowly at −35° C. to a suspension of 224 mg (1.18 mmol) of cuprous iodide in 8 mL of THF. The resulting mixture was stirred for 30 min, and a solution of 125 mg (0.39 mmol) of 3b in 2 mL of THF was added followed by 0.145 mL of BF$_3$Et$_2$O. The mixture was warmed over 5 h to rt with stirring, quenched with 5 ml. of saturated aqueous ammonium chloride solution and extracted with ethyl acetate (3×10 mL). The combined organic phases were dried over $Na_2SO_4$, removal of solvent and column chromatography afforded 54 mg (38%) of 42 and 10 mg (6%) of 43: white solid; mp. 165°–167° C.; $^1$H NMR (270 MHz, $CDCl_3$) δ 7.42 (dm, J=8.3 Hz, 2H), 7.26 (dm, J=8.3 Hz, 2H), 7.23 (m, 1H), 7.09 (m, 4H), 6.00 (ddd, J=9.9, 3.5, 2.7 Hz, 1H), 5.87 (dt, J=9.9, 1.5 Hz, 1H), 4.67 (brt, J=4.7 Hz, 1H), 4.52 (d, J=8.2 Hz, 1H), 4.14 (dd, J=9.0, 6.0 Hz, 1H), 3.65 (q, J=9.0 Hz, 1H), 3.24 (dq, J=8.6, 1.9 Hz, 1H), 2.38 (s, 3H), 1.44 (s, 3H), 1.33 (s, 3H); $^{13}$C NMR (100.6 MHz, $CDCl_3$) δ 142.4 (C), 140.1 (C), 138.6 (C), 134.6 (CH), 129.1 (2CH), 128.61 (2CH), 128.57 (2CH), 127.14 (CH), 126.96 (2CH), 124.2 (CH), 109.93 (C), 77.58 (CH), 72.16 (CH), 58.95 (CH), 47.70 (CH), 27.79 ($CH_3$), 25.83 ($CH_3$), 21.41 ($CH_3$).

Method B: 43 with dilithium diphenylcyanocuprate: a suspension of 161 mg (1.80 mmol) of dry Cu CN in 2 mL of THF was treated with 2.0 mL of 1.8M phenyllithium solution at −78° C. The mixture was warmed to −10° C. with stirring to dissolve CuCN, and then cooled to −78° C., when a solution of 182 mg (0.57 mmol) of 3b was added, followed by 0.221 mL of $BF_3Et_2O$. The mixture was stirred at −78° C. for 3 h and then quenched with 5 mL of aqueous $NH_4Cl$ solution (containing $NH_3$, pH 8). After stirring at rt for 30 min, the mixture was extracted with ethyl acetate (3×15 mL), the combined organic layers were dried over $Na_2SO_4$ and concentrated in vacuo. The residue was chromatographed on silica gel eluting with 10:1 $CHCl_3$/acetone to give 52 mg (23%) of 43.

EXAMPLE 19

43 and (1R, 2R)-N-(6-Hydroxycyclohexa-2,4-dienyl)-(4'-methylphenyl)sulfonamide (24) with phenyltrimethyltin/Pd(0)-catalysis To a degassed solution of compound 3b (80 mg, 0.249 mmol) in DMF (0.8 mL)/$H_2O$ (0.045 mL, 2.5 mmol, 10 eq.) $Pd(CH_3CN)_2Cl_2$ (3.2 mg, 0.012 mmol) was added under argon. After 5 min phenyltrimethyltin (72 mg, 0.30 mmol) was added to the orange solution which decolored to a pale yellow. After 22 h and 37 h phenyltrimethyltin (2×72 mg) was added. When no more 3b remained the reaction mixture became black. After addition of 5 mL of water the mixture was extracted with ether (6x), dried over $Na_2SO_4$, and concentrated. Chromatography (toluene/ethyl acetate, 80:20) afforded 43 (18.6 mg, 19%) and 24 (6.6 mg, 10%): colorless oil; $^1$H NMR (270 MHz, $CDCl_3$) δ 7.78 (dm, J=8.3 Hz, 2H), 7.31 (dm, J=8.0 Hz, 2H), 5.85 (m, 3H), 5.43 (m, 1H), 5.34 (br.d, J=8.3 Hz, 1H), 4.42 (br.d, J=10.6 Hz, 1H), 4.00 (ddm, J=10.6, 8.3 Hz, 1H), 2.90 (br.s, 1H), 2.40 (s, 3H); $^{13}$C NMR (68 MHz, $CDCl_3$) δ 143.8 (C), 137.2 (C), 129.8 (2CH), 129.6 (CH), 127.2 (2CH), 126.5 (CH), 125.6 (CH), 124.0 (CH), 71.2 (CH), 57.1 (CH), 21.5 ($CH_3$).

EXAMPLE 20

(1R,2S,5R,6S)-N-(5,6-Isopropylidenedioxy-2-methylcyclohex-3-enyl)-(4'-methylphenyl)sulfonamide (44)

To a suspension of CuI (7 mg, 0.035 mmol) in anhydrous ether a solution of methylmagnesium bromide (MeMgBr) (0.025 mL, 0.075 mmol) was added at −45° C. and stirred for 30 min. Compound 3b (113 mg, 0.35 mmol) in anhydrous THF (5 mL) was added precooled via cannula and MeMgBr (0.175 mL, 0.525 mmol) was added over 60 min. After 120 min saturated $NH_4Cl$ solution (containing $NH_3$, pH 9) (30 mL) was added to the white suspension and the mixture was extracted with ether (4x). The combined organic phases were washed with brine, dried over $Na_2SO_4$ and concentrated in vacuo. Chromatography (hexane/ethyl acetate, 80:20) afforded 44 (34 mg, 29%): white solid; mp. 112°–113° C.; $[\alpha]_D^{20}$ −54.0° (c=0.58, $CHCl_3$): 1R ($CHCl_3$) 3260, 2980, 2930, 1450, 1375, 1320, 1150, 1080, 1060, 860, 805 cm$^{-1}$; $^1$H NMR (270 MHz, $CDCl_3$) δ 7.80 (dm, J=6.6 Hz, 2H), 7.28 (dm, J=7.9 Hz, 2H), 5.79 (ddd, J=10.0, 3.4, 2.4 Hz, 1H), 5.68 (ddd, J=10.9, 1.9, 0.8 Hz, 1H), 4.66 (d, J=8.7 Hz, 1H), 4.52 (m, 1H), 3.92 (dd, J=8.0, 6.2 Hz, 1H), 3.17 (q, J=9.0 Hz, 1H), 2.41 (s, 3H), 2.07 (m, 1H), 1.24 (s, 3H), 1.17 (s, 3H), 1.14 (d, J=7.2 Hz, 3H); $^{13}$C NMR (100.6 MHz, $CDCl_3$) δ 142.8 (C), 138.8 (C), 136.2 (CH), 129.2 (2CH), 127.3 (2CH), 122.9 (CH), 109.3 (C), 77.5 (CH), 72.2 (CH), 58.8 (CH), 35.75 (CH), 27.5 ($CH_3$), 25.7 ($CH_3$), 21.4 ($CH_3$), 18.0 ($CH_3$); MS (EI) m/z (rel. intensity) 337 (M$^+$) (1.5), 322 (6), 254 (45), 125 (98), 91 (100).

What is claimed:

1. A method for preparing a desired compound of the formula

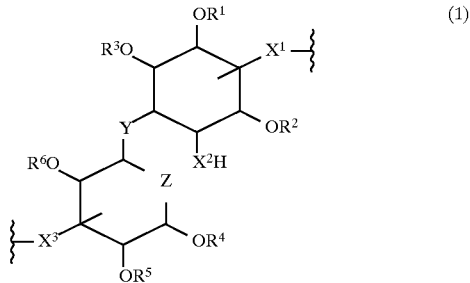

or a carbon or heteroatom conjugate thereof wherein:
$X^1$—$X^3$ independently are O, NH, S, or $CH_2$;
Y is O, $CH_2$, S, or NH;
Z is O, $CH_2$, NH or S; and
$R^1$—$R^6$ independently are H or any suitable alcohol protecting group;
the method comprising:
a) coupling an electrophile of the formula:

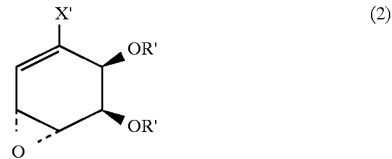

wherein:
X' is H, halogen, CN, alkyl, aryl, or a heteroatom; and each R' is independently any suitable alcohol protecting group, provided that the R' at alcohol C2 and C3 may be the same or different; or by coupling an electrophile of the formula:

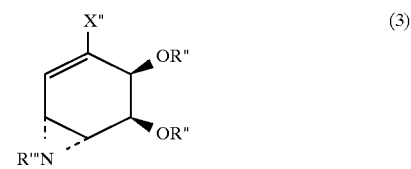

wherein:
X" is H, halogen, CN, alkyl, aryl, or a heteroatom; each R" is independently any alcohol protecting group, provided that the R" at alcohols C2 and C3 may be the same or different; and R'" is H, CBZ, tosyl or any substituted or unsubstituted arylsulfonic acid amide, benzyl or CO₂Me;

with an appropriate nucleophile under suitable conditions;

b) repeating the coupling reaction until the desired compound of formula (1) is obtained; and c) optionally deprotecting the compound of step b).

2. A method of claim 1 comprising coupling an electrophile of formula (2) wherein X' is H, Br, or Cl with a nucleophile comprising an organometallic reagent of the formula RM wherein R is methyl, methylcyclohexyl or phenyl; and M is Mg, Sn, Cu or Pd under suitable conditions.

3. A method of claim 1 comprising coupling an electrophile of formula (3) wherein X" is H, Br, or Cl with a nucleophile comprising an organometallic reagent of the formula RM wherein R is methyl, methylcyclohexyl or phenyl; and M is Mg, Sn, Cu or Pd under suitable conditions.

4. A method of claim 1 wherein the desired compound of formula (1) is selected from the group consisting of a cyclitol conjugate and a carbohydrate conjugate or a semi- or fully carbocyclic analog thereof.

5. A method of claim 1 wherein the desired compound of formula (1) is GM3 (54), silyl Lewis X (56) or a carbon or heteroatom conjugate or either.

6. A method of claim 1 wherein the compound of formula (1) is selected from the group consisting of: (1R,2R,5S,6S)-(4-Chloro-5,6-isopropylidenedioxy-2-methylcyclohex-3-en-1-ol (25); (1R,2R,5S,6S)-(4-Chloro-5,6-isopropylidenedioxy-2-cyclohexylmethylcyclohex-3-en-1-ol (26); (1R,2R,5R,6S)-2,4-Di(cyclohexylmethyl)-5,6-isopropylidenedioxy-cyclohex-3-en-1-ol (27); (1R,5R,6S)-5,6-Isopropylidenedioxy-4,4-diphenylcyclohex-2-en-1-ol (29); (1R,2S,5R,6S)-5,6-Isopropylidenedioxy-4-methylcyclohex-3-en-1-ol (30); (1R,2S,5R,6S)-5,6-Isopropylidenedioxy-2-methylcyclohex-3-en-1-ol (31); (1R,4S,5R,6S)-4-Cyclohexylmethyl-5,6-isopropylidenedioxycyclohex-2-en-1-ol (32); (1R,2R,5R,6S)-2-Cyclohexylmethyl-5,6-isopropylidenedioxycyclohex-3-en-1-ol (33); (1R,2R,5R,6S)-5,6-Isopropylidenedioxy-2-methylcyclohex-3-en-1-ol (35); (1R,2R,5R,6S)-5,6-Isopropylidenedioxy-2-phenylcyclohex-3-en-1-ol (36); (1R,2S,5R,6S)-N-(5,6-Isopropylidenedioxy-2,4-diphenylcyclohex-3-enyl)-(4'-methylphenyl)sulfonamide (37); (1R,5R,6S)-N-(4,4-Diphenyl-5,6-isopropylidenedioxycyclohex-2-enyl)-(4'-methylphenyl) sulfonamide (38); (1R,2R,5R,6S)-N-[2,4-Di(cyclohexylmethyl)-5,6-isopropylidene-dioxycyclohex-3-enyl]-4'-methylphenyl)sulfonamide (39); (1R,2R,5S,6S)-N-(4-Chloro-5,6-isopropylidenedioxy-2-methylcyclohex-3-enyl)-(4'-methylphenyl)sulfonamide (40); (1R,4S,5R,6S)-N-(4-Cyclohexylmethyl-5,6-isopropylidene-dioxycyclohex-2-enyl)-4'-methylphenyl)sulfonamide (41); (1R, 4R,5R,6S)-N-(5,6-Isopropylidenedioxy-4-phenylcyclohex-2-enyl)-(4'-methylphenyl)sulfonamide (42); (1R,2R,5R,6S)-N-(5,6-Isopropylidenedioxy-2-phenylcyclohex-3-enyl)-(4'-methylphenyl) sulfon-amide (43); (1R,2R)-N-(6-Hydroxycyclohexa-2,4-dienyl)-(4'-methylphenyl)sulfonamide (24); and (1R,2S,5R,6S)-N-(5,6-Isopropylidenedioxy-2-methylcyclohex-3-enyl)-(4'-methylphenyl)sulfonamide (44).

7. A compound useful as a synthon, having the formula

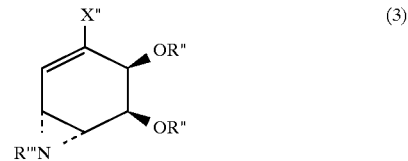

wherein:

X' is H, halogen, CN, alkyl, aryl, or a heteroatom; each R" is independently any alcohol protecting group, provided that the R" at alcohols C2 and C3 may be the same or different; and R'" is H, CBZ, tosylamide or any substituted or unsubstituted arylsulfonic acid amide, benzyl or CO₂Me.

8. The compound of claim 7 which is: (1R,4S,5S,6R)-3-Chloro-4,5-isopropylidenedioxy-7-(4'-methyl-phenyl) sulfonylbicyclo[4.1.0]hept-2-ene (3a); (1R,4R,5S,6R)-3-Bromo-4,5-isopropylidenedioxy-7-(4'-methylphenyl)-sulfonylbicyclo[4.1.0]hept-2-ene (3c); and 1R,4R,5S,6R)-4,5-Isopropylidenedioxy-7-(4'-methylphenyl) sulfonylbicyclo[4.1.0]hept-2-ene (3b).

* * * * *

UNITED STATES PATENT AND TRADEMARK OFFICE
CERTIFICATE OF CORRECTION

PATENT NO. : 5,834,606
DATED : November 10, 1998
INVENTOR(S) : Tomas Hudlicky

It is certified that error appears in the above-identified patent and that said Letters Patent is hereby corrected as shown below:

Title page, the Assignee should read --item

[73] Assignee: Genencor International, Inc.
Rochester, New York
-- Virginia Tech Intellectual Properties, Inc.
Blacksburg, Virginia --

Signed and Sealed this

Twenty-fifth Day of July, 2000

Attest:

Q. TODD DICKINSON

Attesting Officer

Director of Patents and Trademarks